United States Patent
Lubbers et al.

[11] Patent Number: 6,083,244
[45] Date of Patent: Jul. 4, 2000

[54] APPARATUS AND METHOD FOR TENDON OR LIGAMENT REPAIR

[75] Inventors: Lawrence M. Lubbers, Columbus; Kenneth E. Hughes, Gahanna; Carl R. Coleman, Powell, all of Ohio

[73] Assignee: Tendon Technology, Ltd., Loveland, Ohio

[21] Appl. No.: 08/928,866

[22] Filed: Sep. 12, 1997

Related U.S. Application Data

[60] Provisional application No. 60/026,101, Sep. 13, 1996, and provisional application No. 60/043,086, Apr. 8, 1997.

[51] Int. Cl.[7] ............................................. A61B 17/04
[52] U.S. Cl. ..................................... 606/232; 606/233
[58] Field of Search .................................. 606/230, 232, 606/233, 228, 222, 223, 139, 148, 73

[56] References Cited

U.S. PATENT DOCUMENTS

| | | |
|---|---|---|
| 2,075,508 | 3/1937 | Davidson . |
| 2,489,870 | 11/1949 | Dzus ............................. 606/73 |
| 2,760,488 | 8/1956 | Pierce . |
| 3,123,077 | 3/1964 | Alcamo ............................. 606/228 |
| 3,489,143 | 1/1970 | Halloran . |
| 3,664,345 | 5/1972 | Dabbs . |
| 3,716,058 | 2/1973 | Tanner, Jr. ............................. 128/337 |
| 4,549,545 | 10/1985 | Levy ............................. 606/223 |
| 4,590,928 | 5/1986 | Hunt et al. . |
| 4,592,346 | 6/1986 | Jurgutis ............................. 128/92 |
| 4,637,380 | 1/1987 | Orejola ............................. 128/334 |
| 4,643,178 | 2/1987 | Nastari et al. . |
| 4,750,492 | 6/1988 | Jacobs ............................. 606/230 |
| 4,796,612 | 1/1989 | Reese . |
| 4,832,026 | 5/1989 | Jones . |
| 4,873,976 | 10/1989 | Schreiber ............................. 128/334 |
| 4,946,462 | 8/1990 | Watanabe . |
| 4,978,347 | 12/1990 | Ilizarov . |
| 4,988,351 | 1/1991 | Paulos et al. ............................. 606/72 |
| 5,041,129 | 8/1991 | Hayhurst et al. ............................. 606/232 |
| 5,053,047 | 10/1991 | Yoon ............................. 606/223 |
| 5,258,015 | 11/1993 | Li et al. . |
| 5,269,290 | 12/1993 | Barrett et al. ............................. 128/4 |
| 5,269,809 | 12/1993 | Hayhurst et al. . |
| 5,306,290 | 4/1994 | Martins et al. . |
| 5,342,376 | 8/1994 | Ruff . |
| 5,380,334 | 1/1995 | Torrie et al. ............................. 606/104 |
| 5,395,374 | 3/1995 | Miller et al. . |
| 5,417,699 | 5/1995 | Klein et al. ............................. 606/139 |
| 5,464,424 | 11/1995 | O'Donnell, Jr. ............................. 606/228 |
| 5,472,452 | 12/1995 | Trott ............................. 606/232 |
| 5,500,000 | 3/1996 | Feagin et al. . |
| 5,505,735 | 4/1996 | Li ............................. 606/72 |
| 5,520,691 | 5/1996 | Branch . |
| 5,520,700 | 5/1996 | Beyar et al. ............................. 606/139 |
| 5,527,342 | 6/1996 | Pietrzak et al. ............................. 606/232 |
| 5,562,689 | 10/1996 | Green et al. ............................. 606/151 |
| 5,601,557 | 2/1997 | Hayhurst ............................. 606/72 |
| 5,643,320 | 7/1997 | Lower et al. ............................. 606/232 |
| 5,681,352 | 10/1997 | Clancy, III et al. ............................. 606/232 |
| 5,690,632 | 11/1997 | Schwartz et al. ............................. 606/73 |
| 5,707,394 | 1/1998 | Miller et al. ............................. 606/232 |
| 5,707,395 | 1/1998 | Li ............................. 606/232 |
| 5,720,765 | 2/1998 | Thal ............................. 606/232 |
| 5,728,135 | 3/1998 | Bregan et al. ............................. 606/228 |

*Primary Examiner*—Michael Buiz
*Assistant Examiner*—Julian W. Woo
*Attorney, Agent, or Firm*—Wood, Herron & Evans, L.L.P.

[57] ABSTRACT

A device and method for repairing a torn tendon or ligament wherein three incisions are made. A suture is passed from one side of the tear to the other. The suture is tightened to achieve an abutting relationship between the two sides and is secured. A similar product is also shown for use with a flexible suture for repairing bones.

18 Claims, 6 Drawing Sheets

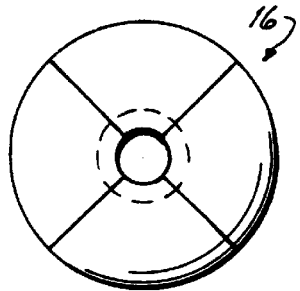
FIG. 7
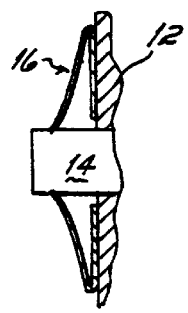
FIG. 8
FIG. 9
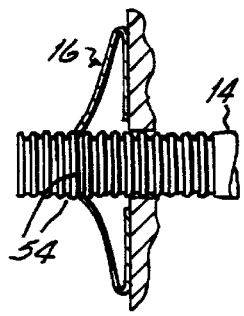
FIG. 10
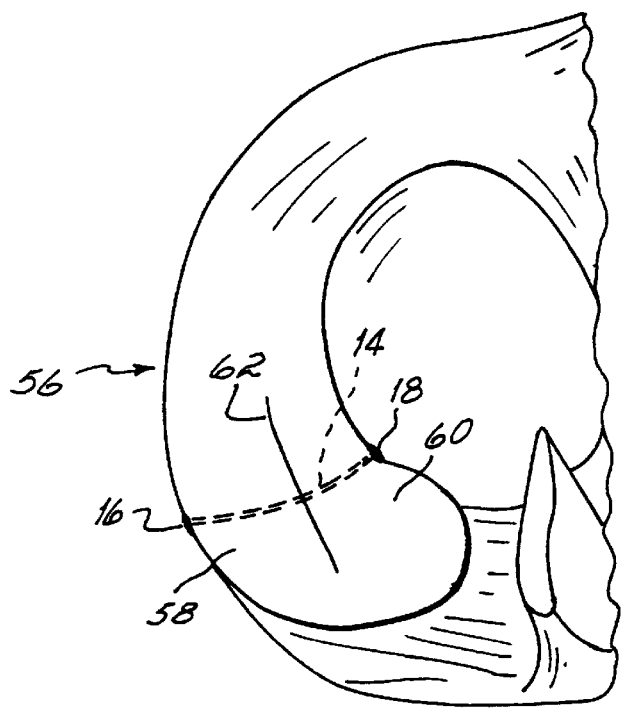
FIG. 11
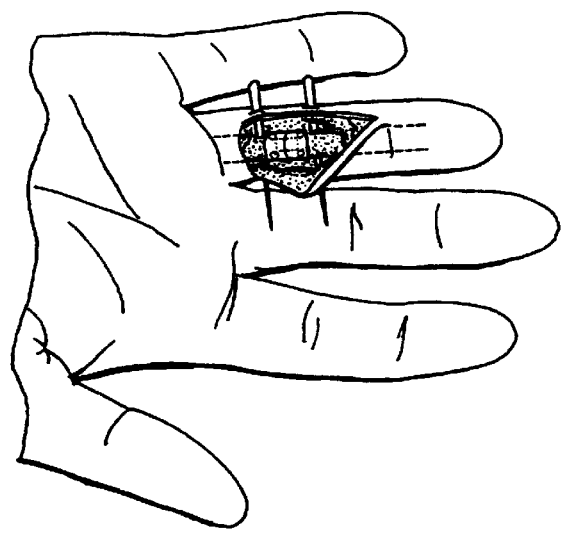
PRIOR ART
FIG. 12

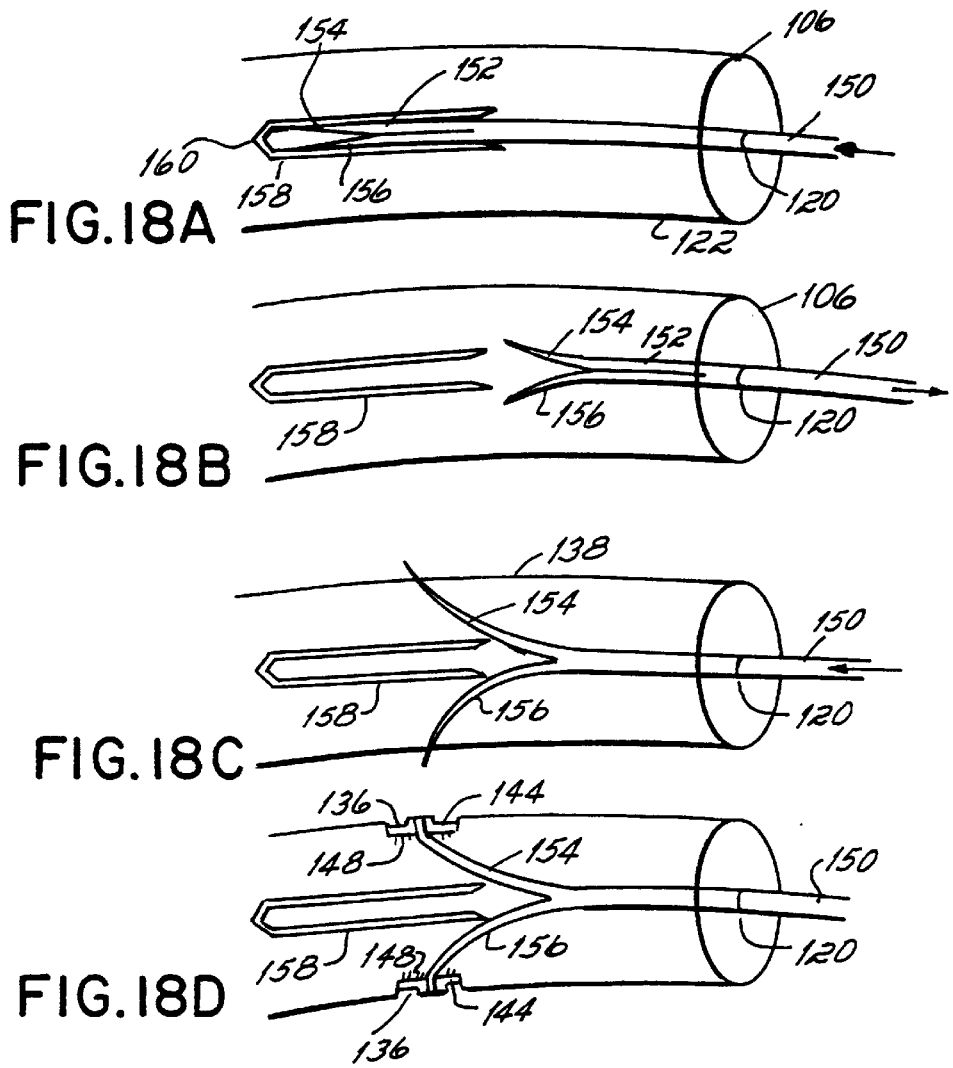
FIG.18A
FIG.18B
FIG.18C
FIG.18D
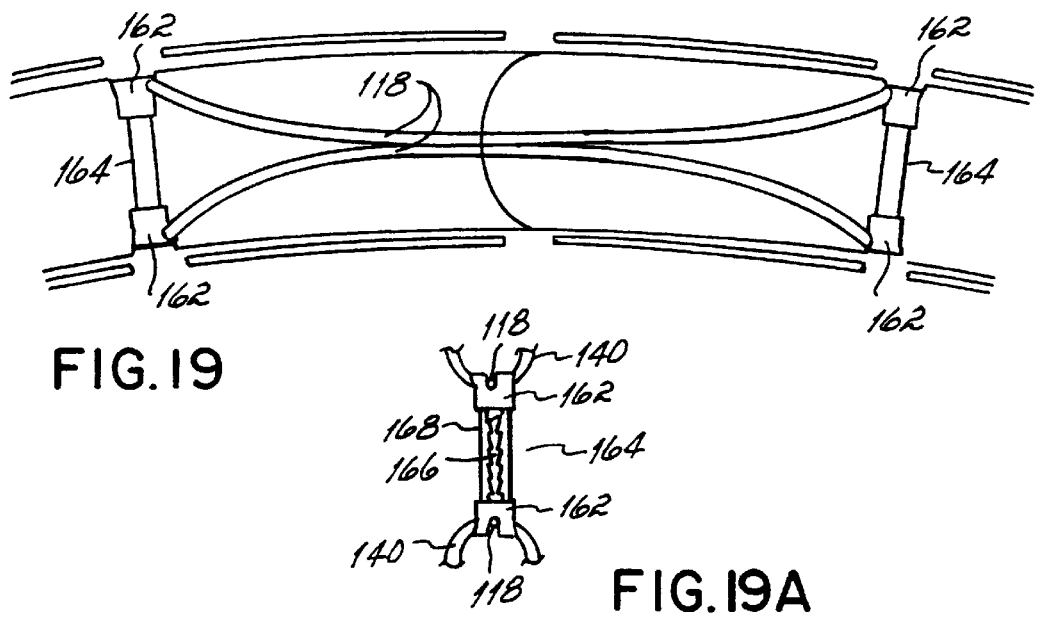
FIG.19
FIG.19A

APPARATUS AND METHOD FOR TENDON OR LIGAMENT REPAIR

This application claims benefit of provisional applicaiton 60/026,101 filed Sep. 13, 1996 also 60/043,086 filed Apr. 8, 1997.

BACKGROUND OF THE INVENTION

1. Field of the Invention

The present invention relates to sutures to repair fractured bones, torn tendons, torn menisci, and the like and more particularly to sutures secured with buttons, locking tabs or other fasteners.

2. Description of the Related Art

Problems associated with failure of flexor tendon/ligament repairs (particularly in the hand) are: breakage of sutures due to their limited tensile strength, weakening of the suture by the knot, excess bulk of the knot, loss of purchase of the suture, and partial or full rupture of the tendon/ligament repair or tearing of the device or material through the collagen fibers. This can result in repeat surgery, increased pain, additional therapy, reduced flexion of the digits due to adhesions, and increased cost, all associated with this very common problem. Strength of the anastomosis is normally based on the strength observed immediately following surgery. However, from the third to twelfth day, softening of the tendon/ligament occurs, and the strength of the repairs decreases.

The repair strength of common two-strand repairs (such as the Kessler stitch shown in FIG. 12) is inadequate, even with an epitendinous horizontal mattress or running-lock suture placed at the anastomosis. In such a repair, the strength after installation is about 2,500 grams, but decreases to about 1,200 grams within one week after surgery. Since this strength can be exceeded by even mild to moderate active tendon/ligament force, it becomes obvious that a more robust tendon/ligament repair method is required. More complex four and six-strand sutures have been tried and demonstrate increased strength of repair, but the difficulty of the anastomosis is greatly increased.

In addition, major disruptions of the tendon/ligament sheath are often required during normal repair of tendon/ligament lacerations. This causes loss of vascularization, and the formation of localized tissue adhesions between the sheath and the tendon/ligament. These adhesions are a form of scar tissue, which interrupts normal motion of the tendon/ligament within the sheath, and prevents full range of motion of the associated joint. Filleting of the sheath to expose the ends of the tendon/ligament for repair disrupts the pulley, causing bowstringing, and is not acceptable technique.

These problems have been known for years, and numerous techniques for internal suturing have been tried. An alternative, external suture device was developed by the present inventors, and, although the strength carrying properties of this device were excellent, the external device was difficult to install and left a large number of suture filaments on the surface of the tendon/ligament. Even though several incremental improvements have been made in the surgical procedures, a truly successful, highly reliable method for repairing small tendons/ligaments in the hand remains to be found.

By most current methods, the ends of the injured tendon/ligament are exposed axially above and below the laceration by separating the tendon/ligament sheath and pulling the tendon/ligament out. Internal/external fixation is applied using manual suturing techniques. The most successful techniques use a mattress, zig-zag or loop-type of suture to place the tensile load further from the laceration and to purchase or gather the tendon/ligament filaments. [The filamentous collagen structure of tendon/ligament lends itself to failure of sutured repairs due to "raking" or tearing apart of the parallel longitudinal fibers]. The primary, load-carrying suture may be preceded or followed by a series of small approximating sutures, placed directly at the interface of the laceration to prevent splaying or misalignment of the tendon/ligament filaments at the site of the wound.

The installed loads (tension and compression) are difficult to control and often the installed suture pulls out of the lacerated tendon/ligament, or fails at a knot, due to either passive or active stress imposed by natural biological loads or by therapy. In addition, slippage of the surgical repair (or misalignment) can result in a gap between the tendon/ligament faces, leading to massive adhesions connected to the tendon/ligament sheath and other adjacent tissues. In addition, adhesions are worsened by opening the tendon/ligament sheath to expose the length of tendon/ligament necessary for most repairs. Using a multiple-windowing technique for flexor tendon/ligament injuries in zones 1 and 2, less damage is incurred to the vincula, tendon/ligament sheath, and pulley structures, reducing adhesions and helping to prevent "bow-stringing."

In a related concept, a primary problem with repair of small bones is their location in a patient's body. The small bones are primarily located in the hands and feet. However, the soft tissue overlying the bones in the hands have a complex anatomy. The primary method currently used to hold the fractured portion together during healing is the screw, or pin, (or combination of these) which has the drawback of having directional rigidity. This increases the problem of precisely aligning the drill holes in order to properly insert the screw or pin and increases the time for performing the procedure.

An additional problem with repairing bones is the tendency for membranes, blood vessels, nerve tissue, and the like, to become wrapped around the filament or wire while the drilling procedure is occurring. There is, thus, a need for a protective bearing surface or mechanized sheath to separate the rotating wire from the other tissues. The sheath would not rotate.

Pierce, U.S. Pat. No. 2,760,488, shows the desirability of drilling through bone with a wire and fastening a button (13) on each side of the bone. However, Pierce requires the use of a threaded button which must be screwed onto the wire.

The patent to Halloran, U.S. Pat. No. 3,489,143, shows the use of a button (23) which is used to increase the tension on a pin (P). The tension is increased by the use of threads on the pin and the button. The button is only found on one side of the fracture line (16).

The patent to Hunt, U.S. Pat. No. 4,590,928, shows a button-like structure which is similar in shape to the present invention. However, the system of operation disclosed in Hunt is substantially different. In Hunt, a hole (24) is drilled in a bone to a depth slightly deeper than the button (10). The button is then inserted in the hole. A stud (20) is then pounded into the recess (16) in the button. The stud extends only slightly further than the button in operation. The buttons are attached to a plate which extends on each side of a fracture, on the same side of the bone (FIG. 11). In an alternative arrangement (shown in FIGS. 16–17), a flexible wire is used with the button, but it is wrapped around the button to secure the wire. Thus, in operation, these buttons and the securing of the bone does not operate in the same way, nor are the structures that similar.

The most relevant patent is the patent to Reese, U.S. Pat. No 4,796,612. Reese shows a pin which is inserted through a bone. The pin has a hook (22) to secure the pin to the bone on one end and on the other end there is a button (26). The button has a ratchet-like protrusion (28) which allows for flexibility in the length of the pin.

SUMMARY OF THE INVENTION

A family of devices is envisioned that would purchase the tendon/ligament remote from the site of repair on a miniature core filament or shaped rod. Such a device would be small enough to be buried within the tendon/ligament fiber elements without causing significant additional bulk at the site of purchase. Yet, by design, it would yield dramatic improvement in pull-out strength compared to standard grasping stitch techniques, such as the Kessler suture.

Such a grasping device or anchor would improve the distribution of stress, would load the inner tendon/ligament fibers remote from the laceration, and should provide strength sufficient for immediate active motion in repaired flexor or extensor tendons or ligaments. The material must be biocompatible such that minimal local reactivity will occur. Long range, it is desirable to utilize one of the modern absorbable polymers, perhaps injection molded or extruded, and drawn, if necessary. However, common nonabsorbable suture materials may suffice, and these provide a simpler means for preliminary efficacy testing.

This invention as applied to the tendon repair has three separate embodiments and our analysis will be separated. A "multiple window" technique has a window or incision at the location of the tendon tear and one or more windows on each side of the tear. In two embodiments, a suture is inserted through the primary window on one side of the tear and exits at the primary window on the other side. The suture(s) pass through the core of the tendon.

In a third embodiment a single suture has a needle on each end and each needle passes through the wound. The needles are directed in opposite directions from the wound to exit at the primary window on one side of the wound.

In the first embodiment, there is a button or other securing means placed at the entrance and exit of the suture. This embodiment includes the internal fixation means as shown in FIGS. 15–16–16A–17–18–19. It is preferable for each of these buttons or other fasteners to have some sort of barbs to aid in securing the button to the tendon. These buttons may also be used to secure a tendon to a bone, by using a button on one end of the filament and a standard bone anchor on the other (FIGS. 21 and 22).

In the second embodiment, a suture includes barbs which are capable of grasping the tendon and securing it in place. The suture is introduced surrounded by a cannula which will keep the barbs from attaching to the tendon prematurely. Once the suture is placed, the cannula is removed (see FIG. 20).

The invention as applied to bone repair consists of two buttons and a flexible or rigid filament. The filament has a rigid segment on at least one end to allow the filament to be drilled into the bone. While the filament is being drilled into the bone, it is preferably surrounded by a sheath. Use of a flexible filament allows for drilling with a greater margin of error, by allowing the filament to bend at the juncture of the fracture. The filament is then tightened and secured at each end (on opposite sides of the bone) by various types of button-like fasteners.

BRIEF DESCRIPTION OF THE DRAWINGS

FIG. 7 is a top view of a third embodiment of a button to be used with the bone repair device of the present invention;

FIG. 8 is a side view of a third embodiment of a button to be used with the bone repair device of the present invention;

FIG. 9 is a sectional view of the third embodiment of a button to be used with the bone repair device of the present invention being attached to a suture;

FIG. 10 is a sectional view of a fourth embodiment of a button to be used with the bone repair device of the present invention being attached to a suture;

FIG. 11 is a perspective view of the bone repair device of the present invention being used to repair a torn or fractured meniscus;

FIG. 12 is a top view of the incisions made in a hand in the prior art to repair a torn tendon;

FIG. 18A is a sectional view of a step in repair of a tendon using a second embodiment of a suture in connection with the second embodiment of the button;

FIG. 18B is a sectional view of a step in repair of a tendon using a second embodiment of a suture in connection with the second embodiment of the button;

FIG. 18C is a sectional view of a step in repair of a tendon using a second embodiment of a suture in connection with the second embodiment of the button;

FIG. 18D is a sectional view of a step in repair of a tendon using a second embodiment of a suture in connection with the second embodiment of the button;

FIG. 19 is a sectional view of a repaired tendon using a third embodiment of the present invention;

FIG. 19A is a sectional view of the button of FIG. 19;

Figure 1:
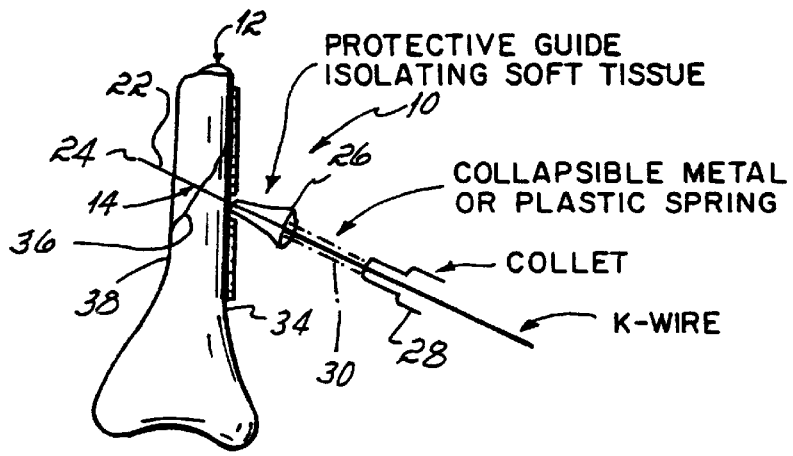
FIG. 1 is a perspective sectional view of the bone repair device according to the present invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other circuit elements where such connection is recognized as being equivalent by those skilled in the art.

DESCRIPTION OF THE PREFERRED EMBODIMENTS

Bone and Meniscus Repair Device

As shown in FIGS. 1–10, a novel device 10 for repairing a fractured bone 12 is shown. The fractured bone repair device 10 has three primary parts, a flexible or rigid suture or filament 14, a first button 16, and a second button 18. First button 16 is ideally identical to second button 18. The suture or filament may be rigid or flexible, monofilament or multifilament.

Figure 2:
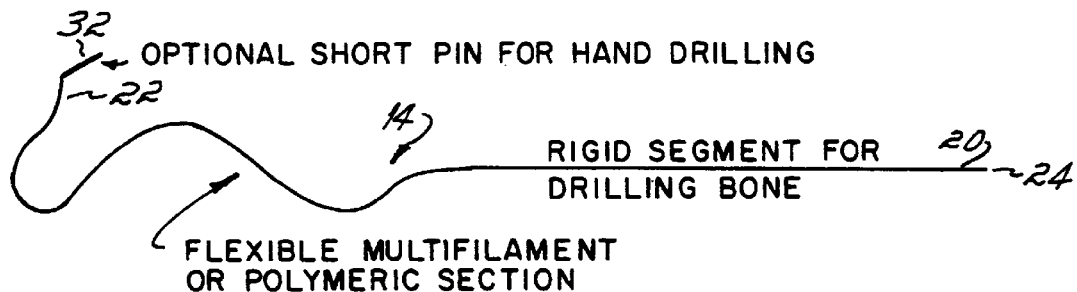
FIG. 2 is a side view of the suture to be used with the bone repair device according to the present invention.
Figure 3:
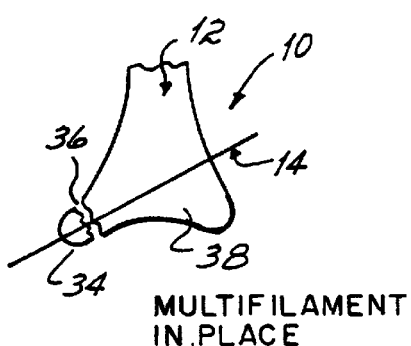
FIG. 3 is a sectional view of the suture in place in a bone to be repaired in accordance with the present invention.
Figure 4:
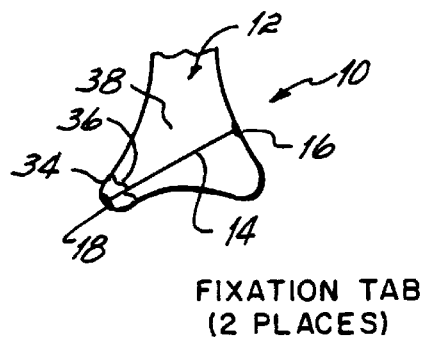
FIG. 4 is a sectional view of a fractured bone repaired with the bone repair device according to the present invention.

As shown most particularly in FIG. 2, suture 14 has a first end 20 and a second end 22. First end 20 of suture 22 is made rigid so as to allow the suture to be drilled through a fractured bone 12, as shown in FIG. 1. The rigid segment 20 is placed in a standard driver (not shown) which is well-known to one of ordinary skill in the art, most preferably a MicroAire Wire Driver. The rigid segment 20 ideally has a sharp point 24 to allow for easier drilling.

A sheath 26 may also be provided for the filament 14 during the drilling procedure and forms a part of this invention. The sheath 26 would serve as an extension from the collet 28 of any of the well-known drilling tools. Two forms are contemplated. The first would use a collapsing sheath (not shown), such as an accordion pleat such that the sheath will buckle as the tool moves towards the bone 12. Alternatively, a concentric spring 30 may be made of any of a variety of materials. The material must be strong enough to withstand any punctures from small bone fragments which may be displaced through the drilling procedure. However, it must be thin enough to allow its collapse as drilling progresses. The material must also have sufficient heat resistance or a sufficiently high melting point that it is unaffected by the heat generated by the drill. The sheath 26 will extend the full length of the drilling tool from the collet 28 to fully protect surrounding tissues.

Optionally a short pin is located on the second end 22 of the suture 14. This pin 32 may be used for hand drilling the bone 12. Whether the bone 12 must be hand-drilled or may be drilled by machine is based on a number of factors, all of which are well-known by these of ordinary skill in the art. The filament may alternately be passed through a pre-drilled hole in the bone 12.

Regardless of how the bone 12 is drilled, the method of operation of the bone repair device 10 is the same. The rigid second end 22 is drilled from a first side 34 of a fracture 36 to a second side 38 of fracture 36. The rigid second end 22 is then pulled such that the suture portion 14 is within the bone 12. The purpose of the suture 14 being optionally flexible is that many bones which are fractured are small in size and are not easily aligned. In order to properly repair a bone, most particularly a small bone, using prior art technology, a practitioner must spend a large amount of time precisely aligning the first side 34 and second side 38 of fracture 36. If the suture used is flexible, the first side 34 and second side 38 need not be precisely aligned, since the flexible suture 14 can bend at any point. While it is desirable that first side 34 and second side 38 be somewhat aligned, it is not necessary to have as great a precision and much time can be saved.

The suture 14 is preferably a monofilament or multifilament wire or flexible polymer. The thickness of suture 14 depends on the size and location of the bone but, for small bones such as are in the hand, will fall within the range of 0.02 to 0.06 inches in diameter. The differing tensile strengths which will be needed for various bones and the tensile strengths of various thicknesses are well-known to one of ordinary skill in the art.

Once the suture 14 has been drilled through bone 12, or passed through a pre-drilled hole, it extends completely through bone 12 from the first side 34 of fracture 36 to the second side 38 of fracture 36. The suture 14 must then be secured in order to hold the first side 34 and second side 38 together until fracture 36 is healed. The suture is secured on each side 34, 36 by a button 16, 18. Because each button 16, 18 is selected from the same group of possible designs, the designs are described only in reference to first button 16. However, it will be understood that second button 18 may have a similar design.

Figure 5:
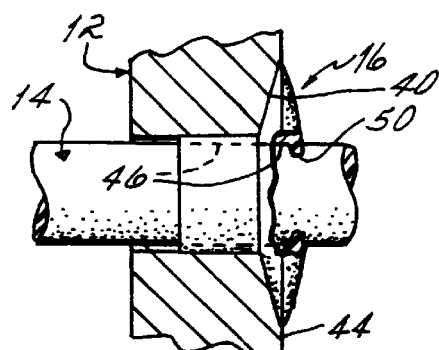
FIG. 5 is a sectional view of a first embodiment of a button to be used with the bone repair device of the present invention.
Figure 6:
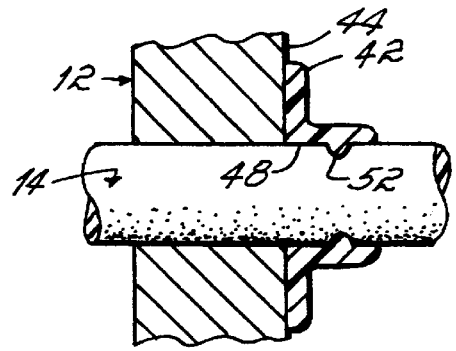
FIG. 6 is a sectional view of a second embodiment of a button to be used with the bone repair device of the present invention.

As is most clearly shown in FIGS. 5 and 6, two types of buttons 16 are preferred. FIG. 5 shows a button 16 which includes a flange 40 which extends to or beneath the surface 44 of bone 12. FIG. 6 shows a button 16 which includes a flange 42 resting on the surface 44 of bone 12. Flanges 40, 42 serve to aid in distributing the tension load from the suture 14. Each button 16 has an inner surface 46, 48 which slidably contacts and circumscribes suture 14. On the inner surfaces 46, 48 of the buttons 16 is one or more notches 50, 52. Notch 50 is formed such that it is an extension of flange 40, whereas notch 52 is formed separately of flange 42. Because suture 14 is flexible and somewhat soft, compared to buttons 16, a crimping tool (not shown) may be used to press inwardly on or crimp button 16 such that notches 50, 52 penetrate suture 14 and become secured to suture 14. In this way, the buttons 16, 18 may become attached to suture 14.

An alternative button 16 is shown in FIGS. 7–10. This button 16 is a locking spring washer. With such a button 16, the tension on the suture 14 may be increased, but not decreased. This type of button 16 locks by itself with no crimping tool required. The suture 14 ideally includes notches or grooves 54 to aid in the attachment of button 16 to suture 14.

This method is ideally designed for use with bones in the hands or feet which are smaller and more delicate. However, the same invention may be used in connection with larger bones and may be particularly useful if a larger bone is broken into many smaller pieces. The diameter of the rigid segment, filament, and pin must be adjusted to effectively join the bone and fragment, especially if the bone and fragment are large.

Turning to FIG. 11, the same invention may also be used to repair a torn meniscus 56. The suture 14 (shown in dashed lines) is threaded through the meniscus 56 from a first side 58 to a second side 60 of fracture or tear 62.

While a meniscus 56 is typically referred to as being torn rather than fractured, the word "fracture" and all forms thereof should be understood to refer to both bones and to menisci in the context of this invention for ease of understanding and vocabulary and to avoid confusion with the invention (described below) which relates to the repair of torn tendons. A first button 16 is attached to and circumscribes suture 14 on a first side 58 of the fracture 62 and a second button 18 is attached to and circumscribes suture 14 on a second side 60 of fracture 62. Buttons 16, 18 may have the same configuration as those described above or may resemble the tabs 144 as described in tendon repair, FIG. 17B.

Tendon Repair Device and Method

The method described may be used with any of the relevant buttons in the present invention. The prior art method for repairing a torn tendon is shown in FIG. 12, and involves making a single long incision over the location of the torn tendon. The present invention (shown in FIG. 13) uses a device and method for repairing a torn tendon through one or more skin incisions and two or more smaller incisions in the sheath, minimizing trauma to critical tissues. This invention may be used to repair either a tendon or a ligament. The term "tendon" as used in the application should be understood to also encompass ligaments.

Figure 13:
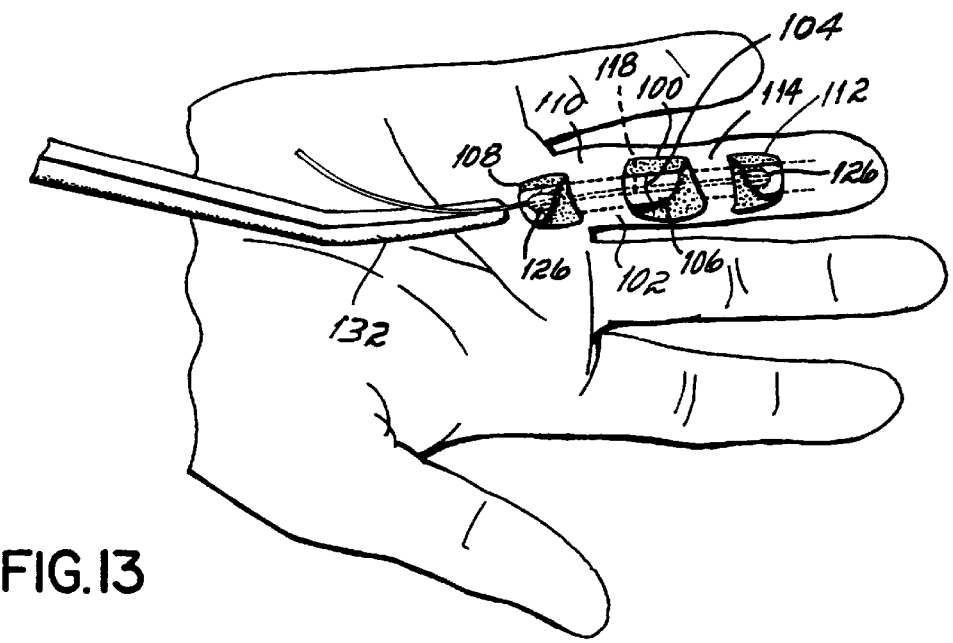
FIG. 13 is a top view of the incisions made in accordance with the present invention to repair a torn tendon.
Figure 14:
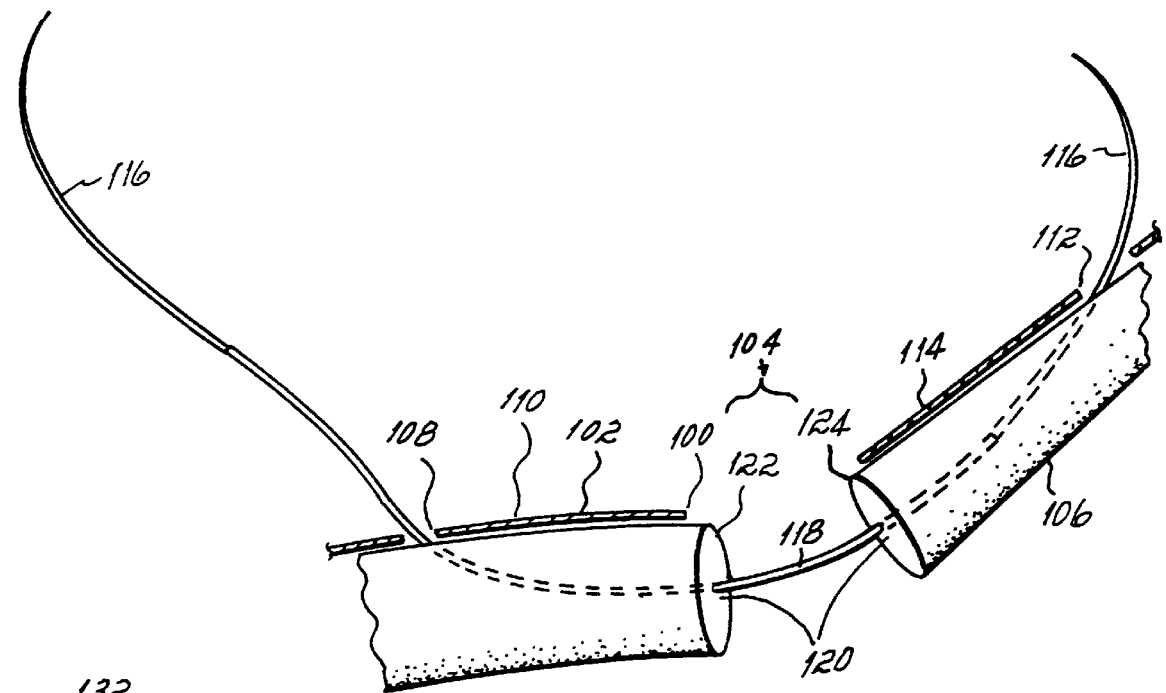
FIG. 14 is a sectional view of a tendon being repaired in accordance with the present invention.

As shown in FIGS. 13 and 14, a surgeon makes a first incision 100 in the skin 102 above the location of the tear 104 in the tendon 106. It is noted that the skin above the tendon tear 104 may have already been incised as in a laceration. If such is the case, only a small neatening of the incision may be relevant. The surgeon then makes a second incision 108 on the first side 110 of the first incision 100. The surgeon also makes a third incision 112 on the second side 114 of the first incision. These incisions 100, 108, 112 preferably involve several transverse incisions or short "T" or "L" incisions. Additional small "window" incisions may be necessary to gain access for retrieval of the tendon end. The incisions 100, 108, 112 may also involve rolling the tendon or ligament sheath down a distance of about 3 mm. A needle 116 (FIG. 14) is then threaded with a core suture or elongate tensile member 118. The needle 116 is preferably a swaged, large radius, non-cutting needle, which allows the needle 116 to penetrate the filamentous tendon 106 without weakening it. For flexor tendons in the hand, the suture 118 is preferably USP size No. 1 or No. 2 and is preferably made of a monofilament of polyester, stainless steel, or polyglactin 910, or other high strength material. The needle 116 and attached suture 118 are then inserted into the tendon at the first side 122 of the tear 104. The needle 116 and the suture 118 travel down the center 120 of the tendon 106, exiting at the second incisions 108. The surgeon then inserts needle 116 and attached suture 118 at approximately the same center 120 of the second side 124 of tear 104. The needle 116 and attached suture 118 exit the tendon 104 through the third incision 112 on the second side 114 of the tear 104. The suture 118 is then tightened such that the first side 122 of the tear 104 is drawn into abutting relationship to the second side 124 of the tear 104, shown most clearly in FIG. 13. A second suture 118 may also need to be inserted in a similar fashion, as will become clear from the following description. Once the suture 118 has been properly placed, it must be secured in order to maintain the abutting relationship between first side 122 and second side 124 of tear 104.

Figure 15:
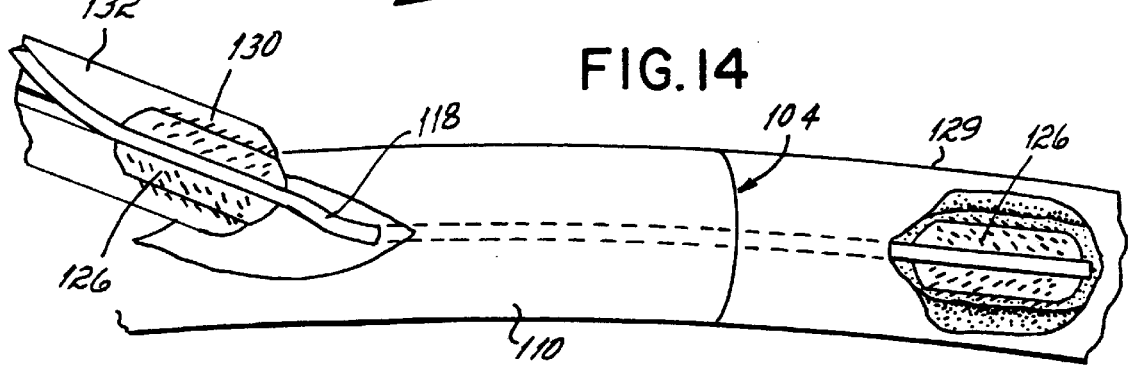
FIG. 15 is a sectional view of a tendon being repaired using a first embodiment of a button.
Figure 15A:
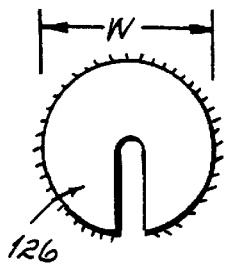
FIG. 15A is a cross-sectional view of a first embodiment of a button as shown in FIG. 15.
Figure 15B:
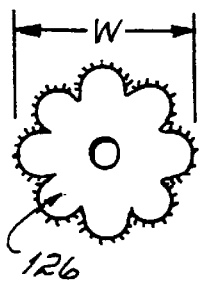
FIG. 15B is a cross-sectional view of a second embodiment of a button as shown in FIG. 15.
Figure 15C:
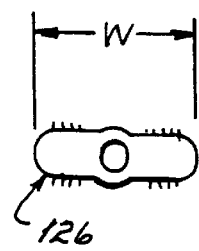
FIG. 15C is a cross-sectional view of a third embodiment of a button as shown in FIG. 15.
Figure 15D:
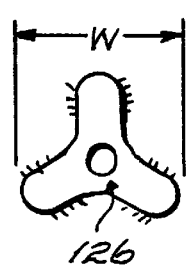
FIG. 15D is a cross-sectional view of a fourth embodiment of a button as shown in FIG. 15.
Figure 16:
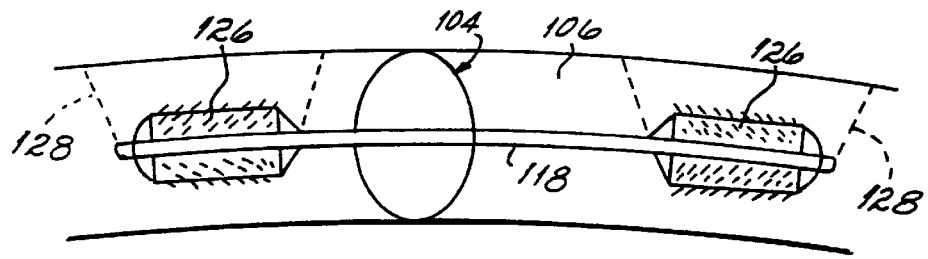
FIG. 16 is a sectional view of a repaired tendon using a first embodiment of a button in accordance with the present invention.
Figure 16A:
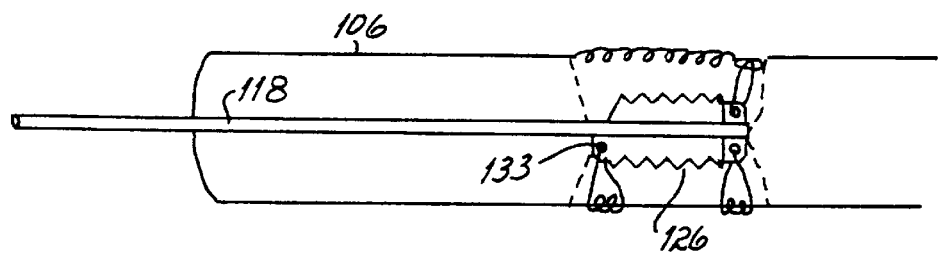
FIG. 16A is a sectional view of a revised stitching procedure in accordance with the invention of FIG. 15.

A first way of securing the suture is with a variety of buttons. A first embodiment is shown in FIG. 15. which shows the use of a sliding anchor button or body 126. A surgeon makes a stab or slit wound 128 in the tendon 106 in an area generally under the second incision 108 made on the first side 110 of the first incision 100. The sliding anchor button or body 126 slips onto the suture 118 and into the stab wound 128 under the exterior surface 129 of tendon 106. The sliding anchor button 126 has burrs 130 which serve to assist in holding sliding anchor button 126 in place in tendon 106 once it reaches the desired location. The burrs 130 are directed such that they are facing towards the tear 104 and generally outwardly from the suture 118 and serve to reduce the possible motion of sliding anchor button 126 and to distribute the axial load. In order to properly place the sliding anchor button 126, a tool 132 should be used which is capable of keeping the exterior surface of sliding anchor button 126 from coming into contact with tendon 106 prior to its correct placement. The tool 132 is important, since otherwise, the burrs 130 can tear or otherwise damage the tendon 106. Once the sliding anchor button 126 is in place, the tool 132 is retracted and sliding anchor button 126 is swaged to the suture 118 such that sliding anchor button 126 is attached to and at least partially circumscribes suture 118. FIGS. 15A–15D show a variety of possible forms for the sliding anchor button 126 in cross section. Each of these sliding anchor buttons 126 has a width W. Preferably width W is about 2 mm. As can be seen in these figures, the sliding anchor button 126 can be configured such that it slides onto suture 118 by being threaded, as in FIGS. 15B–15D, or through a side slot as in FIG. 15A. Note also that in these embodiments, the burrs 130 are directed radially outwardly from the suture. Once the sliding anchor button 126 has been placed and swaged onto suture 118, the stab wound 128 is closed, preferably using a continuous microsuture. As can be seen in FIG. 16A, the stitches used to close the stab wound 128 may also penetrate to sliding anchor button 126 and to optional holes 133. Once one sliding anchor button 126 has been placed, a surgeon can insert a second sliding anchor button in the same way on the second side 114 of the first incision 100 below the third incision 112. During the installation of the second button 126, the abutting relationship between first side 122 and second side 124 of tear 104 is assured by pre-tensioning the core suture 118 as the second button 126 is attached. Tension may be applied by a special aspect of tool 132 or by manual means. The remainder of the procedure is the same as that mentioned above. Once a button has been inserted on each of first side 110 and second side 114, the tendon appears as is shown in FIG. 16. The incisions 100, 108, 112 may then be closed in any fashion known in the art.

Figure 17:
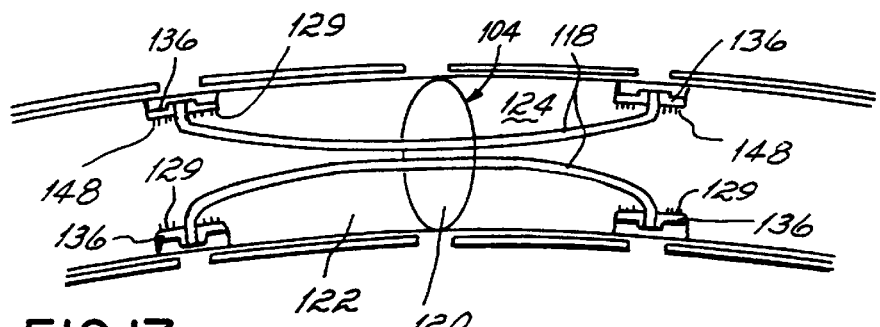
FIG. 17 is a sectional view of a repaired tendon using a second embodiment of a button in accordance with the present invention.
Figure 17A:
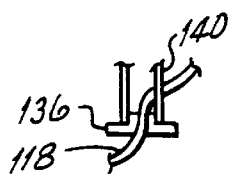
FIG. 17A is a sectional view of a second embodiment of a button in accordance with the present invention being swaged to a suture.
Figure 17B:
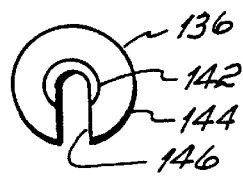
FIG. 17B is a top view of a second embodiment of a button in accordance with the present invention.

A second embodiment of securing buttons is shown in FIG. 17. In FIG. 17, two sutures 118 are used to hold first side 122 and second side 124 in abutting relationship, as was mentioned above. In such a case, a first suture 118 must be placed to one side of the center 120 of tendon 106 and a second suture 118 must be placed to another side of the center 120 of tendon 106. If this embodiment is used, no stab wound need be made in the tendon 106. In this embodiment, once the suture is placed, the tab buttons 136 slide onto suture 118 until they reach the exterior surface 129. The suture 118 may be placed under greater tension by pushing tab buttons 136 such that they place some pressure on the exterior surface 138 of tendon 106. Once the tab buttons 136 have been appropriately placed, they are swaged or crimped to suture 118 such that they are attached to and circumscribe at least a part of suture 118, as shown most clearly in FIG. 17A, by a swaging tool 140. Preferably, as shown in FIG. 17B, the tab button 136 has a circular shape, and includes a central portion 142 and a circular flange 144. The central portion 142 and flange 144 include a slot 146 which allows tab button 136 to be easily placed on suture 118. When tab button 136 is in place, the flange 144 extends radially outwardly of the suture 118, shown most clearly in FIG. 17. The tab button 136 may include burrs 148 which extend generally outwardly from that suture 118 and serve to keep the tab buttons 136 in place and distribute the axial load. Once the first tab button 136 has been placed, a second, third, and fourth tab button 136 may be similarly placed using a similar method for each suture 118.

The tab button 136 may also be used with a different embodiment of the suture, as shown in FIGS. 18A–18D. In this embodiment, a split end monofilament suture 150 is used. The split end suture 150 is inserted in the center 120 of first side 122 of tendon 106, as shown by the direction of the arrow in FIG. 18A. The split end suture 150 has a first end 152. The first end 152 of split end suture 150 is divided into a first part 154 and a second part 156. When split end suture 150 is inserted into tendon 106, the first part 154 and second part 156 are contained within a cap 158 to retain first part 154 and second part 156 together. Cap 158 has a sharp end 160 to allow cap 158 to penetrate tendon 106. After the split end suture 150 and cap 158 reach an appropriate depth, the split end suture 150 is withdrawn in the direction of the arrow shown in FIG. 18B. The split end suture 150 is withdrawn only to just beyond the cap 158. The split end suture 150 is then pushed in an inward direction as noted by the arrow in FIG. 18C. When the split end suture 150 is pushed, the first part 154 and second part 156 split apart and eventually break the exterior surface 138 of tendon 106. A fifth and sixth tab button 136 are then attached to the first part 154 and second part 156, respectively, such that fifth and sixth tab buttons 136 are attached to and at least partially circumscribe the first part 154 and second part 156, respectively. The same operation would apply on the second end (not shown) of the split end suture 150, which is substantially the same as the first end 152 of split end suture 150. The second end would simply be inserted into the second side 124 of tear 104. Other considerations which would be relevant are that the split end suture 150 should ideally be inserted such that half of it extends into each of first side 122 and second side 124, and that first side 122 and second side 124 must be held in an abutting relationship, so that the entire length of the split end suture 150 should be within the tendon 106. The tab buttons 136 used with the split end suture 150 are the same as those mentioned earlier and may include flanges 144 or burrs 148.

Turning now to FIG. 19, a third embodiment of buttons is shown. The transverse button 162 is again used in conjunction with two sutures 118, inserted as described above. The transverse button 162, as shown in FIG. 19A, is attached to and partially circumscribes a first suture 118 and is swaged or crimped onto the first suture 118 with a swaging tool, such as tool 140. Another transverse button 162 is attached to and partially circumscribes a second suture 118 and is swaged or crimped onto the second suture 118 with a swaging tool, such as tool 140. In this embodiment, the transverse buttons 162 are attached to each other by a telescoping mating pin 164. Attached to one of the transverse buttons 162 is the male portion 166 of the pin 164, and attached to the other transverse button 162 is the female portion 168 of the pin 164. The male portion 166 and the female portion 168 are pushed towards each other through tendon 106. When male portion 166 and female portion 168 reach each other, they ratchet and lock, thereby causing one of the transverse buttons 162 to be attached to the other transverse button 162.

Figure 20A:
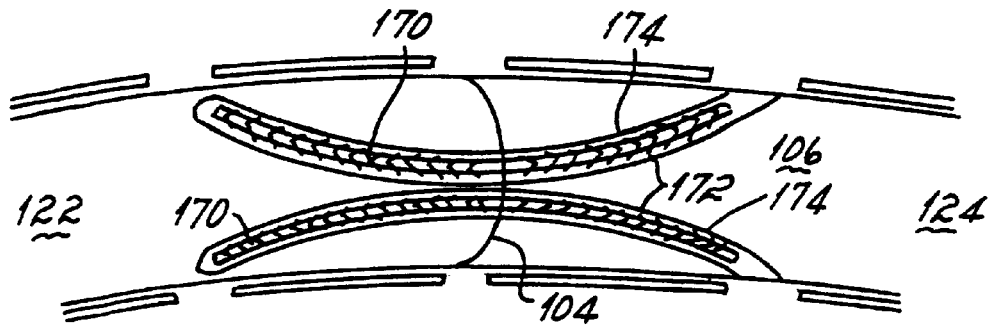
FIG. 20A is a sectional view of a step in the repair of a tendon using a fourth embodiment of the present invention.
Figure 20B:
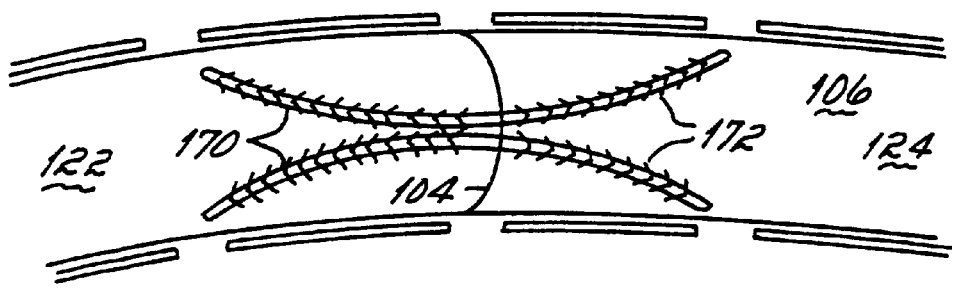
FIG. 20B is a sectional view of a repaired tendon using the fourth embodiment of the present invention.

The second method of securing the suture, instead of using buttons, is by using the suture itself. Turning to FIGS. 20A and 20B, the suture 170 includes barbs 172, which serve to secure the suture 170 and distribute the axial load. When the barbed sutures 170 are inserted into tendon 106 as described above, the sutures must be completely surrounded by a cannula 174 or other protective device which serves to keep barbs 172 from becoming attached to tendon 106 prior to proper placement. Once suture 170 is properly placed, as shown in FIG. 20A, cannula 174 is removed in any standard way. The barbs 172 will then keep the suture 170 in place and keep first side 122 and second side 124 of tear 104 in abutting relationship.

An alternative installation process may be used in this invention where a single suture has a needle on each end. In which case the needles enter the central wound opening and each penetrates the severed end of the tendon; the two needles moving in opposite directions to exit at one of the window openings spaced from the wound. After each needle exits the suture is tightened and the tendon ends are drawn together by the structure and procedural steps described above.

Device for securing a torn tendon to a bone

Figure 21:
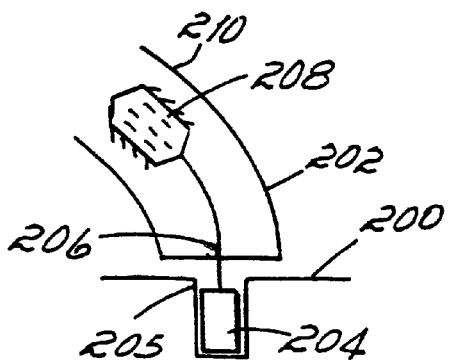
FIG. 21 is a sectional view of a tendon repair device in accordance with the present invention used in connection with a bone anchor.

This invention relates to the use of a button as described above in connection with a known bone anchor in order to secure a tendon to a bone. Turning first to FIG. 21, a system is shown for attaching a bone 200 and a tendon or ligament 202. A bone anchor 204 is installed in a hole 205 in the bone 200. Any of the standard bone anchors known in the art are suitable, as long as they are capable of being attached to a flexible suture 206. As shown in FIG. 21, a sliding anchor button 208 is attached to the flexible suture 206 and at least partially circumscribes the flexible suture 206. The sliding anchor button shown in connection with the bone anchor 204 is inserted as was described earlier in connection with the tendon repair device under the surface 210 of the tendon 202.

Figure 22:
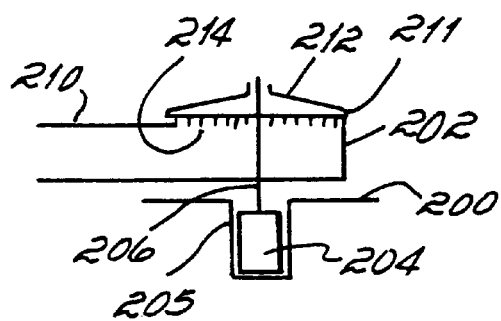
FIG. 22 is a sectional view of a second tendon repair device in accordance with the present invention used in connection with a bone anchor.

Turning now to FIG. 22, a second embodiment of the tendon-bone anchor is disclosed. This embodiment is most preferably used when the tendon has a relatively thin cross-section, such as for exterior tendons and most ligaments. Again, bone anchor 204 is installed in a hole 205 in the bone 200. Any of the standard bone anchors known in the art are suitable, as long as they are capable of being attached to a flexible suture 206. Also attached to the flexible suture 206 is a tab button 212, which includes barbs 214 extending generally parallel with flexible suture 206 and radially outward on flange 211. Tab button 212 is attached to suture 206 as was described above such that tab button 212 is attached to and at least partially circumscribes suture 206.

While certain preferred embodiments of the present invention have been disclosed in detail, it is to be understood that various modifications may be adopted without departing from the spirit of the invention or scope of the following claims.

We claim:

1. Apparatus for repairing a tear in a tendon or ligament, the apparatus comprising:

an elongate tensile member adapted to extend within the interior of said tendon or ligament from a first side of said tear to a second side of said tear;

a first anchor body connected with said elongate tensile member, said first anchor body configured for insertion within the interior of said tendon or ligament;

first securing structure operable to at least assist in holding said first anchor body within the interior of said tendon or ligament on the first side of said tear;

a second anchor body connected for movement along said elongate tensile member, said second anchor body configured for insertion and retention within the interior of said tendon or ligament;

second securing structure operable to at least assist in holding said second anchor body within the interior of said tendon or ligament on the second side of said tear; and locking structure operable to hold said second anchor body at a desired distance from said first anchor body along said elongate tensile member.

2. The apparatus of claim 1, wherein the first and second securing structure comprises projections extending respectively from said first and second anchor bodies generally in a radially outward direction with respect to said elongate tensile member.

3. The apparatus of claim 2, wherein said first and second anchor bodies are tubular-shaped members.

4. The apparatus of claim 1, wherein said first and second anchor bodies are tubular-shaped members.

5. The apparatus of claim 1, wherein the first and second securing structures further comprise portions connected with said first and second anchor bodies, said portions receiving sutures used to secure said first and second anchor bodies within the interior of said tendon or ligament.

6. The apparatus of claim 1 further comprising a tool selectively engageable with at least one of said first and second anchor bodies for inserting said at least one anchor body within the tendon or ligament.

7. The apparatus of claim 1, wherein at least one of said first and second anchor bodies is swageable to said elongate tensile member.

8. The apparatus of claim 1, wherein said first anchor body is connected for movement along said elongate tensile member and further comprising locking structure operable to lock said first anchor body at a desired position along said elongate tensile member.

9. The apparatus of claim 1, wherein the first and second securing structures are integral parts of the respective first and second anchor bodies.

10. A method of repairing a tendon or ligament having a tear, the method comprising:

connecting a first anchor body to an elongate tensile member;

securing said first anchor body within the interior of said tendon or ligament on a first side of said tear;

connecting a second anchor body to said elongate tensile member;

securing said second anchor body within the interior of said tendon or ligament on a second side of said tear;

adjusting the distance between the first and second anchor bodies along said elongate tensile member to bring the first and second sides together at said tear; and holding the first and second sides together at said tear with at least said anchor bodies and said elongate tensile member.

11. The method of claim 10, wherein the steps of securing said first and second anchor bodies further comprise engaging said tendon or ligament with projections on said first and second anchor bodies.

12. The method of claim 11, wherein the steps of securing said first and second anchor bodies further comprise separately suturing said first and second anchor bodies within said tendon or ligament.

13. The method of claim 10, wherein the steps of securing said first and second anchor bodies further comprise separately suturing said first and second anchor bodies within said tendon or ligament.

14. The method of claim 10, wherein adjusting the distance between the first and second anchor bodies further comprises sliding one of said first and second anchor bodies along said elongate tensile member while pulling the first and second sides together with said elongate tensile member under tension.

15. The method of claim 10, wherein at least two spaced apart incisions are made to access said tendon or ligament during said securing and adjusting steps.

16. The method of claim 10 further comprising:

swaging said first and second anchor bodies to said elongate tensile member at the adjusted distance.

17. A method of repairing a tendon or ligament having a tear, the method comprising:

inserting a first anchor body and an elongate tensile member connected therewith through the interior of said tendon or ligament and across said tear;

securing said first anchor body within said tendon or ligament;

connecting a second anchor body to said elongate tensile member;

inserting said second anchor body within said tendon or ligament on an opposite side of said tear from said first anchor body while allowing movement of said second anchor body along said elongate tensile member;

pulling the tendon or ligament together by tensioning the elongate tensile member between said first and second anchor bodies; and fixing said second anchor body on said elongate tensile member at a location which holds the elongate tensile member in tension and holds the tendon or ligament together at said tear.

18. A method of repairing a tendon or ligament having a tear, the method comprising:

connecting a first anchor body to an elongate tensile member;

securing said first anchor body within the interior of said tendon or ligament on a first side of said tear;

securing a second anchor body within the interior of said tendon or ligament on a second side of said tear;

tensioning the elongate tensile member to adjust the distance between the first and second anchor bodies and bring the first and second sides together at said tear; and holding the first and second sides together at said tear with at least said anchor bodies and said elongate tensile member.

* * * * *